US012797154B2

(12) United States Patent
Kok et al.

(10) Patent No.: US 12,797,154 B2
(45) Date of Patent: Nov. 17, 2026

(54) SURGICAL MICROSCOPE SYSTEM AND SYSTEM, METHOD AND COMPUTER PROGRAM FOR A SURGICAL MICROSCOPE SYSTEM

(71) Applicant: LEICA INSTRUMENTS (SINGAPORE) PTE. LTD., Singapore (SG)

(72) Inventors: Alvin Kok, Singapore (SG); John Perng, St. Gallen (CH); Marco Schutz, Singapore (SG)

(73) Assignee: Leica Instruments (Singapore) Pte Ltd., Singapore (SG)

(*) Notice: Subject to any disclaimer, the term of this patent is extended or adjusted under 35 U.S.C. 154(b) by 425 days.

(21) Appl. No.: 17/906,983

(22) PCT Filed: Mar. 17, 2021

(86) PCT No.: PCT/EP2021/056824
§ 371 (c)(1),
(2) Date: Sep. 22, 2022

(87) PCT Pub. No.: WO2021/191022
PCT Pub. Date: Sep. 30, 2021

(65) Prior Publication Data
US 2023/0019054 A1 Jan. 19, 2023

(30) Foreign Application Priority Data
Mar. 24, 2020 (DE) ........................ 102020108074.3

(51) Int. Cl.
*A61B 90/20* (2016.01)
*A61B 3/00* (2006.01)
(Continued)

(52) U.S. Cl.
CPC ............ *A61B 90/20* (2016.02); *A61B 3/0058* (2013.01); *A61B 3/102* (2013.01); *A61B 3/1233* (2013.01)

(58) Field of Classification Search
CPC ...... A61B 3/0058; A61B 8/488; A61B 8/5246
See application file for complete search history.

(56) References Cited

U.S. PATENT DOCUMENTS 5,497,775 A * 3/1996 Nonaka ................. G01S 7/5205 600/438
5,993,391 A * 11/1999 Kamiyama ............ A61B 8/463 600/443
(Continued)

FOREIGN PATENT DOCUMENTS

EP 2684525 A1 1/2014
JP 2013111124 A 6/2013
(Continued)

*Primary Examiner* — Pascal M Bui Pho
(74) *Attorney, Agent, or Firm* — 2SPL Patent Attorneys PartG mbB; Yong Beom Hwang

(57) ABSTRACT

Examples relate to a surgical microscope system, and to a system, a method and a computer program for a surgical microscope system. The system comprises one or more processors and one or more storage devices. The system is configured to obtain intraoperative sensor data of at least a portion of an eye from a Doppler-based imaging sensor of the surgical microscope system. The system is configured to process the intraoperative sensor data to determine information on a blood flow within the eye. The system is configured to generate a visualization of the blood flow. The system is configured to provide a display signal to a display device of the surgical microscope system based on the visualization of the blood flow within the eye.

16 Claims, 5 Drawing Sheets

(51) Int. Cl.
*A61B 3/10* (2006.01)
*A61B 3/12* (2006.01)

(56) References Cited

U.S. PATENT DOCUMENTS

| | | | | |
|---|---|---|---|---|
| 8,926,515 | B2 * | 1/2015 | Ragauskas | A61B 8/4209 600/561 |
| 2005/0171438 | A1 * | 8/2005 | Chen | G01B 9/0201 600/425 |
| 2010/0256488 | A1 * | 10/2010 | Kim | A61B 8/06 600/439 |
| 2014/0063458 | A1 * | 3/2014 | Imamura | G06V 40/19 382/134 |
| 2015/0297062 | A1 * | 10/2015 | Golenberg | A61B 1/00048 348/68 |
| 2017/0238798 | A1 | 8/2017 | Isogai | |
| 2018/0161051 | A1 * | 6/2018 | Humayun | A61B 8/10 |
| 2018/0279874 | A1 | 10/2018 | Yoshida | |
| 2020/0064118 | A1 * | 2/2020 | Fujimoto | A61B 5/7425 |
| 2021/0196120 | A1 * | 7/2021 | Puyo | A61B 3/0025 |

FOREIGN PATENT DOCUMENTS

| | | | |
|---|---|---|---|
| JP | 2016116595 | A | 6/2016 |
| JP | 2017136213 | A | 8/2017 |
| JP | 2019164347 | A | 9/2019 |
| JP | 2019213859 | A | 12/2019 |

* cited by examiner

SURGICAL MICROSCOPE SYSTEM AND SYSTEM, METHOD AND COMPUTER PROGRAM FOR A SURGICAL MICROSCOPE SYSTEM

TECHNICAL FIELD

Examples relate to a surgical microscope system, and to a system, a method and a computer program for a surgical microscope system.

BACKGROUND

Glaucoma is a group of diseases characterized by progressive atrophy of the optic nerve head leading to visual field loss, and ultimately, blindness.

Glaucoma is often associated with elevated intraocular pressure (TOP), which is the most important risk factor for visual field loss progression because it damages the optic nerve fibers via multiple mechanisms. In a "normal" eye, intraocular pressure ranges from 10 to 21 mm mercury. In an eye with glaucoma, the pressure can rise to as much as 75 mm mercury. The TOP may be the only treatable aspect of glaucoma and its successful reduction is effective in slowing the progression of the disease.

Aqueous shunts or glaucoma drainage devices are increasingly utilized in the management of refractory glaucoma. The traditional glaucoma surgeries (trabeculectomy and glaucoma drainage devices), while very effective, are associated with risks such as double vision, devastating eye infections, exposure of a drainage implant, swelling of the cornea, and excessively low TOP. Although these risks are relatively infrequent, they make most surgeons delay glaucoma surgery until all other less invasive treatment options are maximized (medications and laser treatment) and the patient has definitive glaucoma worsening.

MIGS (Minimally Invasive Glaucoma Surgery) procedures have been developed in recent years to reduce some of the complications of most standard glaucoma surgeries. These procedures have a higher safety profile with fewer complications and a more rapid recovery time than other invasive techniques. The majority of the MIGS approaches targets an outflow of aqueous humor from the trabecular meshwork, suprachoroidal space or subconjunctival layer.

SUMMARY

There may be a desire for providing an improved concept for a surgical microscope for use in glaucoma surgery.

This desire is addressed by the subject-matter of the independent claims.

Examples of the present disclosure are based on the finding, that key steps in MIGS procedures includes properly identifying the trabecular meshwork (the landmark seen on gonioscopy), avoiding undue outward pressure, and confirming proper placement of devices or ablation instruments. A poor view due to corneal folds, excessive bleeding, and a shallow chamber make the procedure challenging for surgeons. The learning curve for a single stent placement may be considered challenging for glaucoma surgeons doing their initial cases due to poor vision through the microscope and gonioscope. It is another finding that another major gap in glaucoma surgical treatment is the surgeon's understanding of outflow dynamics. The above-presented MIGS approaches try to improve aqueous outflow to lower the TOP in the eye. Other systems may provide no modality that allows surgeons to intra-operatively visualize aqueous flow patterns, and that aids the surgeons in the customization of the placement and location of MIGS devices, to target high flow or low flow vasculatures.

Examples of the present disclosure thus provide a system, method and computer program for a surgical microscope system, and a corresponding surgical microscope system, that processes intraoperative sensor data of the eye from a Doppler-based imaging sensor, determines the blood flow within the eye based on the intraoperative sensor data, generates a visualization of the blood flow, and outputs the visualization to the surgeon, to aid in the placement of the stent by the surgeon.

Embodiments of the present disclosure provide a system for a surgical microscope system. The system comprises one or more processors and one or more storage devices. The system is configured to obtain intraoperative sensor data of at least a portion of an eye from a Doppler-based imaging sensor of the surgical microscope system. The system is configured to process the intraoperative sensor data to determine information on a blood flow within the eye. The system is configured to generate a visualization of the blood flow. The system is configured to provide a display signal to a display device of the surgical microscope system based on the visualization of the blood flow within the eye. Doppler imaging enables the generation of sensor data that indicates the blood flow within the eye, which is processed and presented to the surgeon, thus assisting the surgeon during eye, and in particular glaucoma, surgery.

In various embodiments, the visualization is generated such, that the blood flow is highlighted using one or more colors within the display signal. For example, the one or more colors may be used to contrast the blood flow from imagery of the tissue, and/or to distinguish blood flow at different depths within the eye.

In some embodiments, the system is configured to determine an amount of the blood flow based on the intraoperative sensor data. The visualization may be generated such that the amount of the blood flow is visualized within the display signal. The amount, or velocity, or the blood flow may provide a good intra-operative marker of a potential stent position.

For example, the system may be configured to determine a direction of the blood flow based on the intraoperative sensor data. The visualization may be generated such that the direction of the blood flow is visualized within the display signal. The direction of the blood flow is another factor that can be considered when placing the stent.

In some embodiments, the system may be configured to obtain intraoperative three-dimensional sensor data of a plurality of layers of the eye from a further sensor of the surgical microscope system. The system may be configured to determine the plurality of layers of the eye within the intraoperative three-dimensional sensor data. The system may be configured to assign the blood flow to the plurality of layers of the eye. The visualization may be generated such, that blood flow within different layers is distinguishable within the visualization. Thus, both the vertical position of the blood flow among the layers, and the tissue structure may be shown to the surgeon.

For example, the system may be configured to obtain the intraoperative three-dimensional sensor data from an optical coherence tomography (OCT) sensor of the surgical microscope system. OCT can be used to provide intraoperative three-dimensional sensor data, e.g. for eye surgery.

In various embodiments, the visualization of the blood flow may be merged with or overlaid on visual sensor data (e.g. camera sensor data) of the eye. Accordingly, the system may be configured to obtain intraoperative visual sensor data of the eye from an optical imaging sensor of the surgical microscope system/The system may be configured to determine an alignment between the intraoperative sensor data and the intraoperative visual sensor data. The system may be configured to provide the display signal to the display device based on the alignment between the intraoperative sensor data and the intraoperative visual sensor data. Thus the visualization of the blood flow may be shown together with the intraoperative visual sensor data.

For example, the system may be configured to overlay the visualization over the intraoperative visual sensor data. The system may be configured to provide the display signal comprising the intraoperative visual sensor data with the overlaid visualization to the display device. This may provide the surgeon with a combined view, without requiring the surgeon to mentally co-locate the intraoperative visual sensor data and the visualization of the blood flow.

In various embodiments, the system is configured to provide the visualization without the intraoperative visual sensor data to the display device. For example, the visualization may be overlaid over a purely optical image of the surgical site.

In some embodiments, the intraoperative sensor data is intraoperative sensor data from a Power Doppler imaging sensor. Power Doppler sensors are more sensitive than Color Doppler Imaging sensors, but may provide no information about the direction of flow.

Alternatively or additionally, the intraoperative sensor data may be intraoperative sensor data from a Color Doppler Imaging (CDI) sensor. CDI may be used to measure a velocity (and thus amount) of the blood flow, and a direction of the blood flow, with less sensitivity than Power Doppler Imaging.

Embodiments of the present disclosure further provide a surgical microscope system comprising the system, a Doppler-based imaging sensor, and a display device.

In some embodiments, as shown above, the Doppler-based imaging sensor may be a Color Doppler Imaging sensor. Alternatively, the Doppler-based imaging sensor may be a Power Doppler sensor. In a third variant, the surgical microscope system may comprise both a Color Doppler Imaging sensor and a Power Doppler sensor. For example, the Doppler-based imaging sensor may be configured generate the intraoperative sensor data via a probe to be brought in contact with the eye. Probes are used as part of the setup of a Doppler-based imaging sensor.

In some embodiments, the Doppler-based imaging sensor may comprise a range control modality for adjusting the penetration depth of ultrasound emitted by the Doppler-based imaging sensor. The system may be configured to control the range control modality to adapt a depth of the intraoperative sensor data. This may allow the system to either image the near the surface of the surgical site or deeper into the tissue.

Embodiments of the present disclosure further provide a method for a surgical microscope system. The method comprises obtaining intraoperative sensor data of at least a portion of an eye from a Doppler-based imaging sensor of the surgical microscope system. The method comprises processing the intraoperative sensor data to determine information on a blood flow within the eye. The method comprises generating a visualization of the blood flow. The method comprises providing a display signal to a display device of the surgical microscope system based on the visualization of the blood flow within the eye.

Embodiments of the present disclosure further provide a computer program with a program code for performing the method when the computer program is executed on a processor.

SHORT DESCRIPTION OF THE FIGURES

Some examples of apparatuses and/or methods will be described in the following by way of example only, and with reference to the accompanying figures, in which FIGS. 1*a* and 1*b* show schematic diagrams of examples of a system for a surgical microscope system;

FIG. 1*c* shows a schematic diagram of an example of a surgical microscope system;

FIGS. 1*d* to 1*e* show schematic diagrams of different visualizations of blood flow within an eye;

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
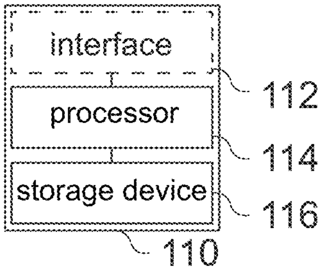
Figure 1B:
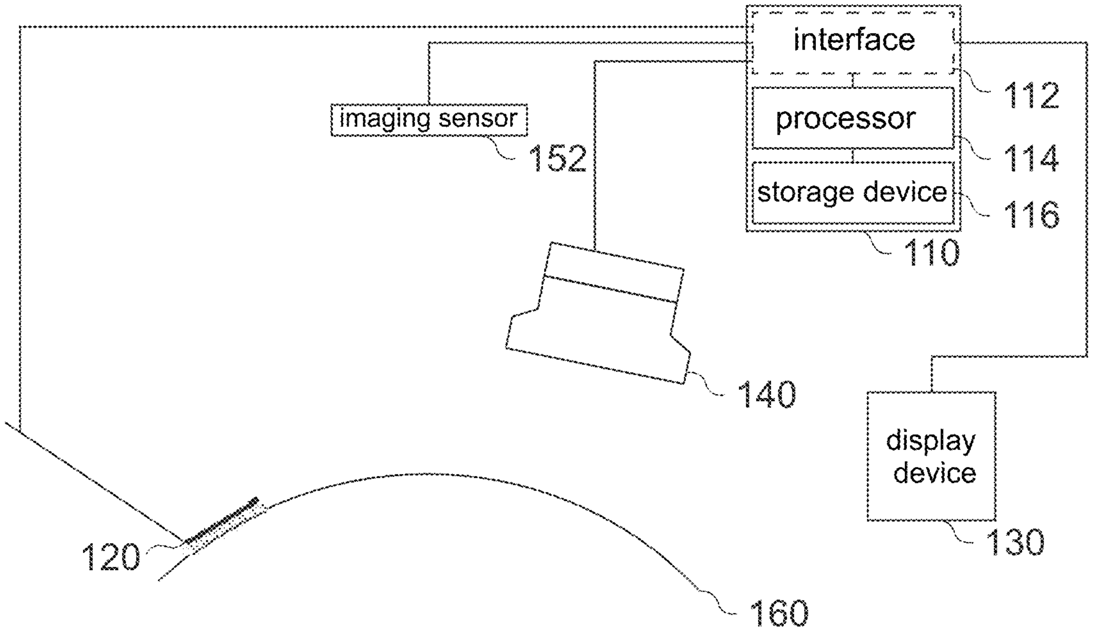

FIGS. 1*a* and 1*b* show schematic diagrams of examples of a system 110 for a surgical microscope system 100. The system 110 comprises one or more processors 114 and one or more storage devices 116. Optionally, the system comprises an interface 112. The one or more processors are coupled to the one or more storage devices and to the optional interface. In general, the functionality of the system is provided by the one or more processors, e.g. in conjunction with the optional interface and/or the one or more storage devices. The system is configured to obtain intraoperative sensor data of at least a portion of an eye 160 from a Doppler-based imaging sensor 120 of the surgical microscope system 100, e.g. via the interface 112. The system is configured to process the intraoperative sensor data to determine information on a blood flow within the eye. The system is configured to generate a visualization of the blood flow. The system is configured to provide a display signal to a display device 130 of the surgical microscope system (e.g. via the interface 112) based on the visualization of the blood flow within the eye.

Figure 1C:
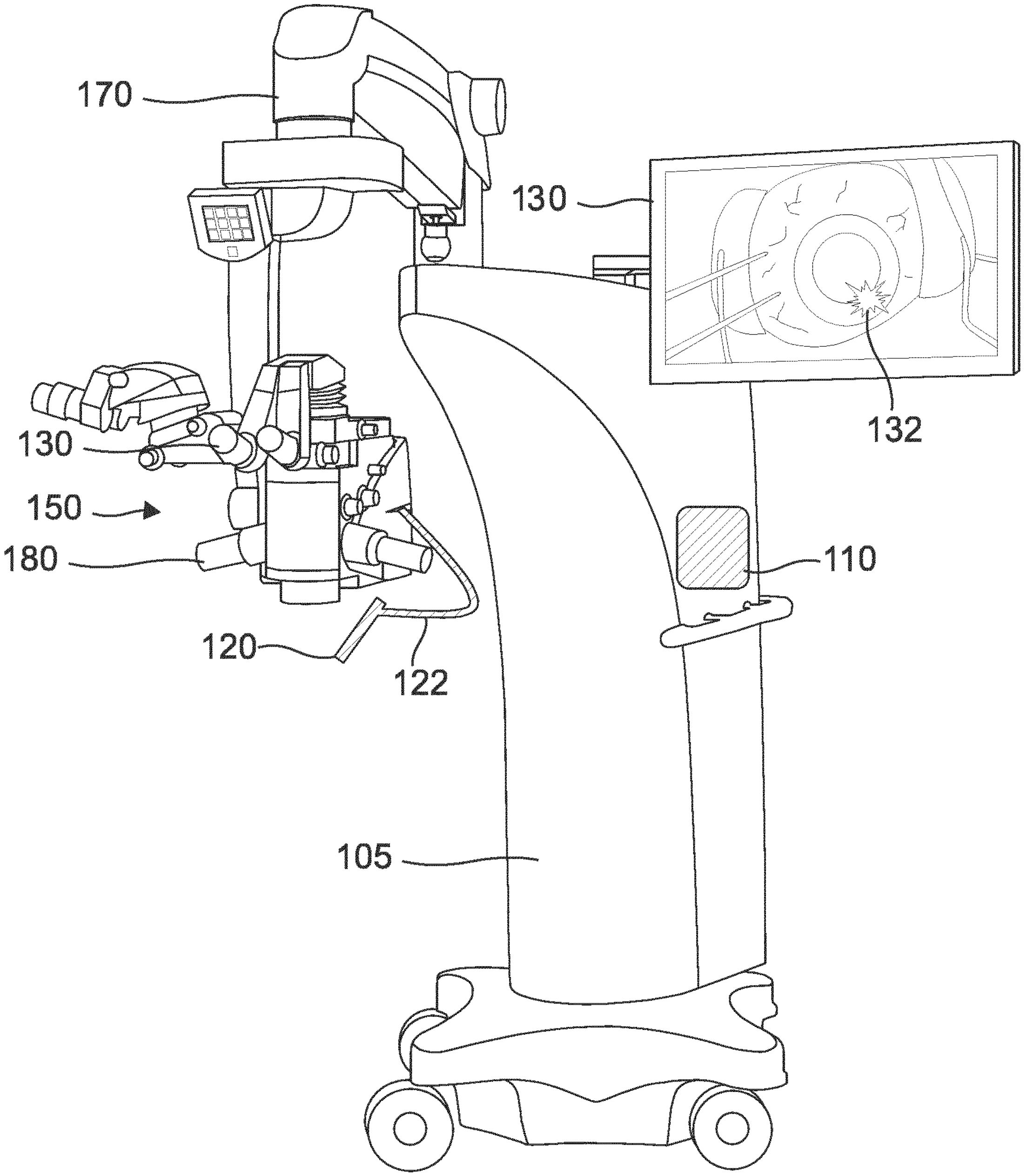

Examples of the present disclosure relate to a system, method and computer program for a surgical microscope system, and to a corresponding surgical microscope system, that uses intraoperative sensor data of a Doppler-based imaging sensor to generate a visualization of a blood flow within an eye during surgery. In general, a microscope, such as the microscope 150 (or "optics carrier") shown in FIG. 1*c*, is an optical instrument that is suitable for examining objects that are potentially too small to be examined by the human eye (alone). For example, a microscope may provide an optical magnification of a sample. In modern microscopes, the optical magnification is often provided for a camera or an imaging sensor, such as an imaging sensor 152 of the microscope 150, as shown in FIG. 1*b*. Alternatively, a purely optical approach may be taken. The microscope 150 may further comprise one or more optical magnification components that are used to magnify a view on the sample, such as an objective (i.e. lens). In the context of this application, the term "(surgical) microscope system" is used, in order to cover the portions of the system that are not part of the actual microscope (which comprises optical components), but which are used in conjunction with the microscope, such as the system 110, the Doppler-based imaging sensor 120 or the display device 130.

FIG. 1*c* shows a schematic diagram of an example of a surgical microscope system 100 (i.e. a microscope system for use during surgery) comprising the system 110. The surgical microscope system further comprises at least one Doppler-based imaging sensor 120, and the display device 130. In FIG. 1*c*, the (doppler) probe of the Doppler-based imaging sensor 120 is attached to the surgical microscope 150 via flexible arm 122. The microscope system shown in FIG. 1*c* is a surgical microscope system for use in ophthalmology surgery, i.e. eye surgery. The surgical microscope system 100 shown in FIG. 1*c* comprises a number of optional components, such as a base unit 105 (comprising the system 110) with a (rolling) stand, a (robotic or manual) arm 170 which holds the microscope 150 in place, and which is coupled to the base unit 105 and to the microscope 150, and steering handles 180 that are attached to the microscope 150. One or more of the display devices may be part of the microscope 150, e.g. as auxiliary or as ocular displays. For example, the system 110 may comprise or implement the doppler transceiver (of the Doppler-based imaging sensor), range control of the Doppler-based imaging sensor and signal digitalizer of the Doppler-based imaging sensor. On the auxiliary display 130 and/or in the ocular displays, the visualization 132 of the blood flow may be shown as color overlay.

There are a variety of different types of microscopes. If the microscope is used in the medical or biological fields, the sample being viewed through the microscope may be a sample of organic tissue, e.g. arranged within a petri dish or present in a part of a body of a patient. Examples of the present disclosure relates to a surgical microscope and surgical microscope system for use in eye surgery. Therefore, the sample, or sample of organic tissue, is the eye 160, or at least the portion of the eye, of the patient.

The system is configured to obtain intraoperative sensor data of at least a portion of an eye 160 from the Doppler-based imaging sensor 120 of the surgical microscope system 100. In general, Doppler-based (ultrasound) imaging is a technique that is based on ultrasound imaging. In "classical" ultrasound imaging, also known as pulse-echo ultrasound imaging, a pulse is transmitted into the tissue, and the amplitude and round-trip time of the echo is used together with knowledge about the directionality of the pulse to generate a depth image of the tissue. In Doppler-based imaging (or Doppler-based ultrasound imaging), instead of (or in addition to) the amplitude of the echo, the Doppler-shift of the echo is used to determine the velocity of the tissue or fluid relative to the Doppler probe. Doppler-based ultrasound imaging is used to measure the blood flow within vessels, such as the heart, arteries and veins, or to determine a movement of tissue, such as heart walls.

There are various types of Doppler-based imaging sensors. A first type of Doppler-based (ultrasound) imaging sensor is a sensor called a "Color Doppler Imaging Sensor", which is often used to visualize blood flow in arteries or veins, as it supports the determination of a direction of the blood flow. For example, the intraoperative sensor data may be intraoperative sensor data from a Color Doppler Imaging sensor. The Doppler-based imaging sensor may be a Color Doppler Imaging sensor. In color doppler imaging (also called Color Flow Imaging, CFI), the Doppler-based imaging sensor may be configured to generate an estimate of the velocity of tissue or of a liquid (e.g. blood) based on a phase shift between echoes of subsequent pulses returning from a given volume of the sample. Alternatively, a difference in the time delay between echoes returning from a given volume of the sample may be used to estimate the velocity. In CDI, as introduced in the early 1980s, the velocity of the movement might only be measured along the direction of the pulses emitted by the ultrasound probe. In more advanced sensor configurations, such as the ones that may be used in examples, if the directionality of the blood flow is desired, the direction of the blood flow may be determined by changing an angle of the emitted ultrasound pulses, e.g. using beam-forming. Accordingly, the intraoperative sensor data of the Color Doppler Imaging sensor may comprise information on a velocity and/or a direction of movement of a blood flow within the eye.

Another type of Doppler-based (ultrasound) imaging is Power Doppler Imaging. In Power Doppler Imaging, instead of analyzing the velocity and/or direction of the movement of the tissue or liquid, the strength of the Doppler signal is visualized. For example, the Doppler-based imaging sensor of the surgical microscope system may be a Power Doppler sensor. The intraoperative sensor data may be intraoperative sensor data from a Power Doppler imaging sensor. The Power Doppler sensor may be configured to determine the magnitude of a doppler shift at a given volume of the sample. Accordingly, the intraoperative sensor data of the Color Doppler Imaging sensor may comprise information on a strength (or power) of movement of a blood flow within the eye. While Power Doppler imaging might not provide information on a directionality or velocity of the blood flow, its sensitivity may be higher than the sensitivity of CDI.

In some embodiments, both Doppler imaging techniques may be combined. For example, intraoperative sensor data may comprise both intraoperative sensor data from a Power Doppler imaging sensor and intraoperative sensor data from a Color Doppler Imaging sensor.

Both types of sensors use a probe that is brought into contact with the eye (via a gel). The probe comprises an ultrasound emitter (or at least an emission modality for emitting ultrasound pulses generated by a pulse generator), and a sensor (or at least a portion of the sensor that is brought into contact with the eye). Accordingly, the Doppler-based imaging sensor may be configured generate the intraoperative sensor data via a probe to be brought in contact with the eye. In some embodiments, the Doppler-based imaging sensor may be a separate sensor (or separate sensors, if both types of the Doppler-based imaging sensors are used). Alternatively, the functionality of the Doppler-based imaging sensor(s) may be implemented by the system 110.

In various embodiments of the present disclosure, the intraoperative sensor data may comprise image data, e.g. frames of two-dimensional image data. For example, in the image data, the tissue of the eye may be shown as greyscale image, and a Doppler-based visualization of the blood flow may be shown superimposed (e.g. in color) over the greyscale image. Alternatively, the intraoperative sensor data may comprise two sets of image data, one showing the tissue of the eye (e.g. based on pulse-echo-ultrasound imaging) and the other one showing the Doppler-based visualization of the blood flow. If two types of Doppler-based imaging sensors are used image data from both sensors may be comprised in the intraoperative sensor data. Alternatively, the intraoperative sensor data may comprise raw data, e.g.

raw data related to the amplitude and/or phase of one or more echoes to pulses emitted by an ultrasound emitter, e.g. together with an angle of the pulses emitted by the ultrasound emitter relative to the probe.

The sensor data being obtained from the Doppler-based imaging sensor is intraoperative sensor data, i.e. sensor data that is generated during surgery. For example, the intraoperative sensor data may be obtained and processed during surgery. In other words, the system may be configured to perform real-time processing of the intraoperative sensor data during the surgery on the eye. Accordingly, the system may be configured to provide the display signal to the display device during surgery, e.g. in real-time (i.e. with a pre-fined maximal delay relative to the corresponding intraoperative sensor data).

The system is configured to process the intraoperative sensor data to determine information on the blood flow within the eye. As has been laid out above, the intraoperative sensor data may comprise information on the blood flow within the eye, e.g. information on the strength (or power) of movement of the blood flow within the eye, information on the direction of the blood flow within the eye, and/or information on the amount of the blood flow within the eye. The intraoperative sensor data may comprise the respective sensor data for a plurality of different positions of at least the portion of the eye. For example, if the intraoperative sensor data comprises image data, each pixel of the image data may comprise information on the blood flow for a position of the plurality of different positions of the portion of the day. The system may be configured to process the intraoperative sensor data to extract the information on the blood flow within the eye from the intraoperative sensor data, e.g. for the plurality of position of the portion of the eye. For example, the system may be configured to process the colors (the colors being indicative of the direction, velocity and/or strength of the blood) being visible within the image data to extract the information on the blood flow within the eye from the intraoperative sensor data, or to process the raw data to extract the information on the blood flow within the eye from the intraoperative sensor data. In any case, the system may be configured to determine the amount of the blood flow based on the intraoperative sensor data. Additionally or alternatively, the system may be configured to determine the direction of the blood flow based on the intraoperative sensor data. After processing, the system may have compiled the information on the blood flow for each of the plurality of positions of the portion of the eye.

Subsequently, the system generates a visualization of the blood flow for the plurality of positions of the portion of the eye. In other words, the system is configured to generate a visualization of the blood flow. In some embodiments, different symbols may be used to visualize the blood flow, e.g. vector arrows to indicate the direction, bolder arrows for a higher amount of blood flow, longer arrows for a higher velocity etc. Alternatively or additionally, different colors may be used to visualize the blood flow. In other words, the visualization may be generated such, that the blood flow is highlighted using one or more colors within the display signal. For example, the visualization is generated such, that the direction of the blood flow is visualized within the display signal, e.g. such, that different directions are highlighted using different colors. Additionally or alternatively, the visualization may be generated such, that the amount of the blood flow is visualized within the display signal. For example, the visualization may be generated such, that different amounts (or velocities) of blood flow are highlighted using different colors. For example, a visualization may be generated, wherein a first direction of the blood flow is indicated by a first range of colors (e.g. black to red) and a second direction of the blood flow is indicated by a second range of colors (e.g. black to blue), and wherein the color within the range of colors represents the amount and/or velocity of the blood flow in the respective direction. Alternatively, a visualization may be chosen with four directions, and four color ranges (e.g. black to yellow, green, blue and red).

Figure 1D:
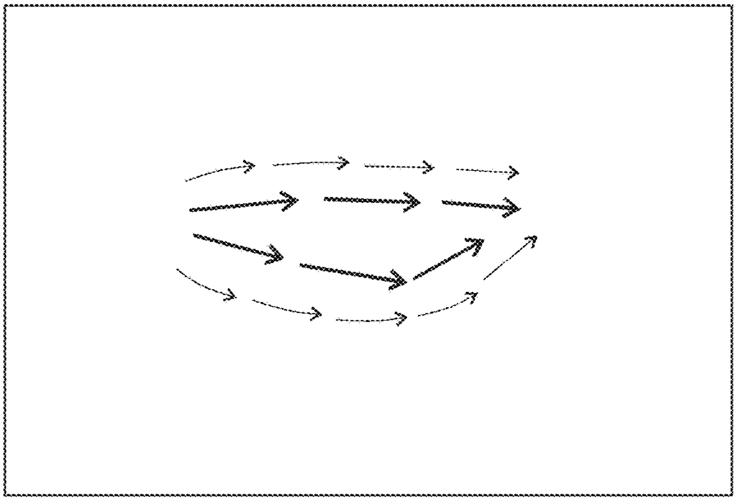
Figure 1E:
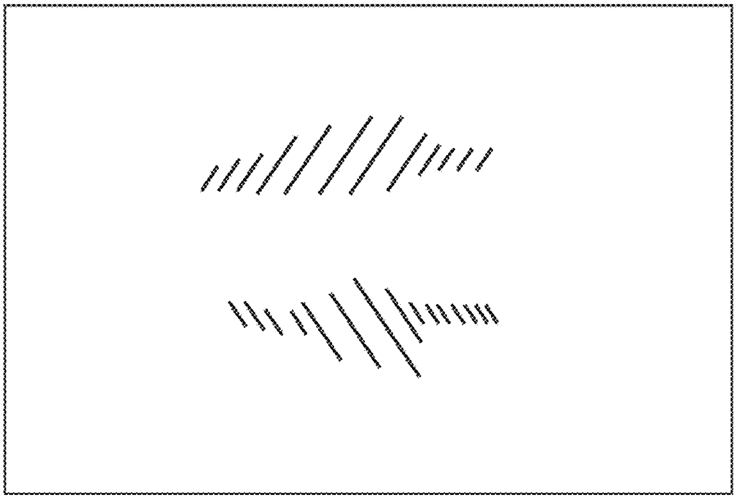

FIGS. 1*d* to 1*e* shows schematic diagrams of different visualizations of blood flow within an eye. In FIG. 1*d*, the direction of the blood flow is visualized using arrows, with the thickness of the arrows indicating the amount of blood, and the length of the arrows indicating the velocity. In FIG. 1*e*, the direction of the blood flow is visualized using different patterns, which represent different range of colors, with the amount of the blood flow being visualized using different density patterns, which represent different colors within the ranges of colors.

In some embodiments, the blood flow at different depths may be distinguished. For example, the eye may comprise a plurality of different layers, with blood flow occurring at one or several layers of the plurality of layers. The system may thus identify the plurality of layers, and assign the determined blood flow to the respective layer the blood flow occurs at. Accordingly, the system is configured to obtain intraoperative three-dimensional sensor data of a plurality of layers of the eye from a further sensor 140 (or alternatively or additionally from the Doppler-based imaging sensor) of the surgical microscope system (e.g. via the interface 112). For example, the system may be configured to obtain the intraoperative three-dimensional sensor data from an optical coherence tomography (OCT) sensor 140 of the surgical microscope system. Accordingly, the surgical microscope sensor may comprise an optical coherence tomography sensor 140. Alternatively, the system may be configured to transform the underlying pulse-echo ultrasound sensor data of the Doppler-based imaging sensor into three-dimensional sensor data to obtain the intraoperative three-dimensional sensor data, e.g. by extracting the plurality of layers from the pulse-echo ultrasound sensor data.

The system may be configured to determine the plurality of layers of the eye within the intraoperative three-dimensional sensor data. For example, the intraoperative three-dimensional sensor data may comprise a three-dimensional representation of the tissue of the portion of the eye. The system may be configured to identify layers within the three-dimensional representation of the tissue of the portion of the eye, and to determine the plurality of layers based on the layers that are identified within the three-dimensional representation of the tissue of the portion of the eye.

The system may be further configured to assign the blood flow to the plurality of layers of the eye. To determine, at which depth below the surface of the eye the blood flow occurs, the penetration depth of the ultrasound pulses that are used for the Doppler-based imaging sensor may be adapted to the different layers of the plurality of layers. Accordingly, the Doppler-based imaging sensor may comprise a range control modality, e.g. a control circuitry, for adjusting the penetration depth of ultrasound emitted by the Doppler-based imaging sensor (e.g. by the emitter of the probe of the Doppler-based imaging sensor). This may allow the system to either image the near the surface of the surgical site or deeper into the tissue. The system may be configured to control the range control modality to adapt a depth of the intraoperative sensor data. For example, the system may be configured to control the range control modality such, that the depth of the intraoperative sensor data is aligned with the layers of the plurality of layers. For example, the system may be configured to control the range control modality such, that the penetration depth of ultrasound emitted by the Doppler-based imaging sensor is sequentially targeted at each of the plurality of layers, to obtain intraoperative sensor data representing the blood flow in each of the plurality of layers. The visualization may be generated such, that blood flow within different layers is distinguishable within the visualization. For example, blood flow at different layers may be represented by different colors. In other words, the system may be configured to generate the visualization such that the blood flow at different layers is represented by different colors The system is configured to provide the display signal to the display device 130 of the surgical microscope system based on the visualization of the blood flow within the eye. For example, the display device may be an ocular display of the surgical microscope 150, or an auxiliary display that is arranged at the surgical microscope or at the base unit of the surgical microscope system.

Figure 3:
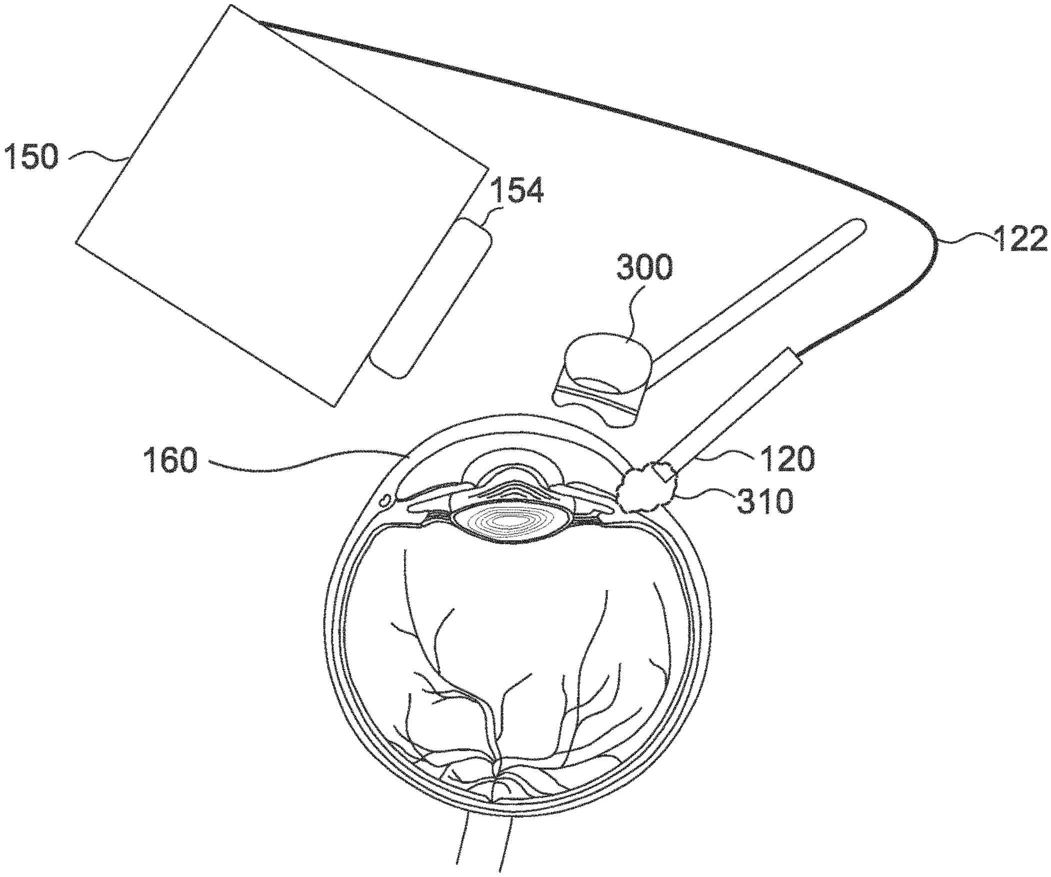
FIG. 3 shows a schematic diagram of different sensors and modalities being used in glaucoma surgery.
Figure 4:
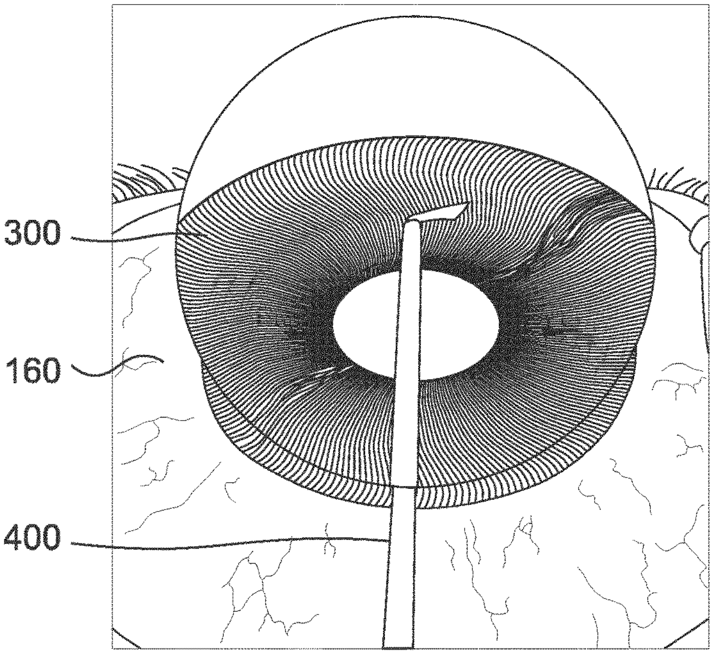
FIG. 4 shows a schematic diagram of a view on an eye through a gonioprism.

As, in some embodiments, the probe of the Doppler-based imaging sensor can be moved on the surface of the eye, the intraoperative sensor data may be aligned the with visual perception of the portion of the eye, e.g. to provide an accurate overlay within the oculars, or to generate a visualization that comprises both a visual representation of the surface of the eye and the visual representation of the blood flow, correctly overlapped. For example, the system may be configured to obtain intraoperative visual sensor data of the eye from an optical imaging sensor 152 of the surgical microscope system (e.g. from an optical imaging sensor 152 of the surgical microscope 150 of the surgical microscope system), via the interface 112. For example, the optical imaging sensor 152 may comprise or be an APS (Active Pixel Sensor)—or a CCD (Charge-Coupled-Device)-based imaging sensor. For example, as shown in FIGS. 3 and 4, the optical imaging sensor may be configured to generate the intraoperative visual sensor data via a gonioprism (a prism that can be used to re-direct the optical path between the optical imaging sensor and the eye, so the optical imaging sensor of the surgical microscope system can generate the intraoperative visual sensor data from the side).

The system may be configured to determine an alignment between the intraoperative sensor data and the intraoperative visual sensor data. As has been introduced before, the intraoperative sensor data may comprise image data. In the image data, the tissue of the eye may be shown as greyscale image, and a Doppler-based visualization of the blood flow may be shown superimposed (e.g. in color) over the greyscale image. Alternatively, the intraoperative sensor data may comprise two sets of image data, one showing the tissue of the eye (e.g. based on pulse-echo-ultrasound imaging) and the other one showing the Doppler-based visualization of the blood flow. The system may be configured to determine the alignment between the tissue of the eye shown in the image data and the intraoperative visual sensor data. For example, the system may be configured to extract contours of the tissue of the eye from the image data and from the intraoperative visual sensor data. The system may be configured to align the contours with each other, e.g. using contour pattern matching. For example, the system may be configured to perform image/pattern recognition of the vascular tortuosity and thickness, combined with depth information (e.g. of the intraoperative sensor data). For example, the system may be configured to perform translation, rotation and/or deformation of the contours to align the contours with each other (e.g. based on the shape of the gonioprism). Once the visual intraoperative sensor data is aligned with the intraoperative sensor data, the system knows the position of the intraoperative sensor data relative to the eye. This information may also be used to align the intraoperative sensor data with the intraoperative three-dimensional sensor data. In other words, the system may be configured to align the intraoperative sensor data with the intraoperative three-dimensional sensor data, e.g. based on the alignment between the visual intraoperative sensor data and the intraoperative sensor data, or similar to the alignment being performed between the visual intraoperative sensor data and the intraoperative sensor data.

The system may be configured to provide the display signal to the display device based on the alignment between the intraoperative sensor data and the intraoperative visual sensor data. In some embodiments, the surgeon may be provided with a view on the sample that is camera-based, i.e. in which the surgical microscope is used to generate the visual intraoperative sensor data, which is then presented to the surgeon via displays that are integrated within the oculars of the surgical microscope. In this case, the visualization may be overlaid on the intraoperative visual sensor data, and the resulting image may be presented to the surgeon via the display device. In other words, the system may be configured to overlay the visualization over the intraoperative visual sensor data, and to provide the display signal comprising the intraoperative visual sensor data with the overlaid visualization to the display device. Additionally or alternatively, the system may be configured to overlay the visualization over a visual representation of the intraoperative three-dimensional sensor data, and to provide the display signal comprising the visual representation of the intraoperative three-dimensional sensor data with the overlaid visualization to the display device, e.g. as a three-dimensional representation of the blood flow and the tissue.

Alternatively, the alignment between the intraoperative sensor data and the intraoperative visual sensor data might merely be used to determine the placement of the visualization relative to the eye. In some embodiments, the view on the eye through the surgical microscope may be an optical view, without involving an imaging sensor. Merely the visualization may be superimposed on the optical view, e.g. using a transparent display or via a one-way mirror. The system may be configured to provide the visualization without the intraoperative visual sensor data to the display device. The display device may be configured to overlay the visualization over the optical view of the eye. The placement of the visualization relative to the optical view on the eye may be based on the alignment between the intraoperative sensor data and the intraoperative visual sensor data.

The interface 112 may correspond to one or more inputs and/or outputs for receiving and/or transmitting information, which may be in digital (bit) values according to a specified code, within a module, between modules or between modules of different entities. For example, the interface 112 may comprise interface circuitry configured to receive and/or transmit information. In embodiments the one or more processors 114 may be implemented using one or more processing units, one or more processing devices, any means for processing, such as a processor, a computer or a programmable hardware component being operable with accordingly adapted software. In other words, the described function of the one or more processors 114 may as well be implemented in software, which is then executed on one or more programmable hardware components. Such hardware components may comprise a general-purpose processor, a Digital Signal Processor (DSP), a micro-controller, etc. In at least some embodiments, the one or more storage devices 116 may comprise at least one element of the group of a computer readable storage medium, such as an magnetic or optical storage medium, e.g. a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the system and of the surgical microscope system are mentioned in connection with the proposed concept or one or more examples described above or below (e.g. FIGS. 2 to 5). The system and of the surgical microscope system may comprise one or more additional optional features corresponding to one or more aspects of the proposed concept or one or more examples described above or below.

Figure 2:
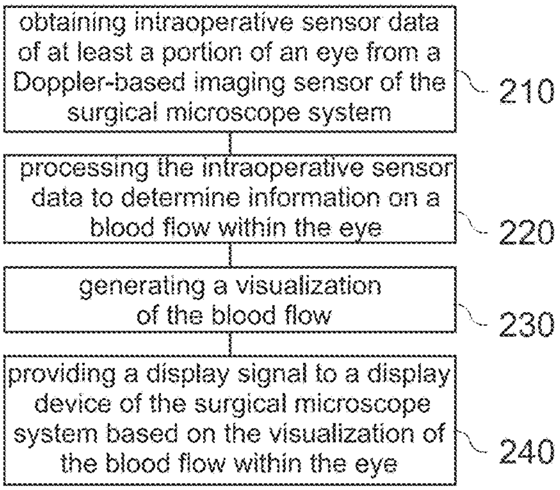
FIG. 2 shows a flow chart of a method for a surgical microscope system.

FIG. 2 shows a flow chart of a corresponding method for a surgical microscope system, e.g. for the surgical microscope system 100 of FIGS. 1*a* to 1*e*. The method comprises obtaining 210 intraoperative sensor data of at least a portion of an eye from a Doppler-based imaging sensor of the surgical microscope system. The method comprises processing 220 the intraoperative sensor data to determine information on a blood flow within the eye. The method comprises generating 230 a visualization of the blood flow. The method comprises providing 240 a display signal to a display device of the surgical microscope system based on the visualization of the blood flow within the eye.

As indicated above, features described in connection with the system 110 and the surgical microscope system 100 of FIGS. 1*a* to 1*e* may be likewise applied to the method of FIG. 2.

More details and aspects of the method are mentioned in connection with the proposed concept or one or more examples described above or below (e.g. FIG. 1*a* to 1*e*, 3 to 5). The method may comprise one or more additional optional features corresponding to one or more aspects of the proposed concept or one or more examples described above or below.

Various embodiments of the present disclosure relate to integrated doppler imaging (e.g. as provided by the system of FIGS. 1*a* to 1*e*) for vascular visualization in microscopy (e.g. using a Doppler microscope). Color Doppler imaging (CDI) or power Doppler can be used to access flow velocities, in particular, when integrated into the microscope system can be used to provide assessment of ocular blood flow. This can be particularly useful for a more accurate stent placement and intra-operative confirmation of aqueous outflow.

Another application would be as a non-invasive method to detect retinal anomalies such as retinal detachment. The retina is supplied with blood by the central retinal artery which enters the optic nerve about 1 cm behind the eye and then divides into an upper and lower branch. Each of these arteries then further divides into the superior and inferior nasal arterioles and the superior and inferior temporal arterioles, which also further branches out along the retinal surface.

Doppler microscopy may be useful to detect blood flow in these retinal membranous structures which provides real-time visual confirmation if a detachment has occurred and/or if the retinal is fully affixed after the surgical procedure. It can also be used intraoperatively to identify highly vascularized retinal or choroidal sites in the peripheral retina which can be used as grafts for transplantations during surgery for better clinical outcomes. Another application of the doppler microscope is to identify sites of metastasis within the eye. Such eye cancers, such as choroidal metastasis, are most commonly associated with heavily vascularized areas feeding the cancerous tumor. Doppler imaging can be used intraoperatively to identify such sites and act as a clinical confirmation post-surgery that all tumorous tissues have been treated. While doppler imaging of the eye has been studied in literature, the technologies are not yet integrated into microscopy for intra-operative surgical use in ophthalmology.

Color Doppler Imaging (CDI) uses the principle of Doppler shift in frequency, in Hertz, to measure the blood flow velocity in cm/sec. The advantage of CDI is that it is non-invasive, not affected by poor ocular media, requires no contrast or radiation and has been proven in ophthalmology in imaging the ocular blood flow. CDI measures the blood flow velocity, and this can be used as a good intra-operative marker of a potential stent position within a given vessel during surgery.

Power Doppler is more sensitive than CDI for the detection and demonstration of blood flow, but provides no information about the direction of flow. It has however, higher sensitivity to detect minimal blood flow, and can be used to obtain images that are difficult or impossible to obtain using standard color Doppler with a better edge definition and depiction of continuity of flow. Power Doppler is particularly useful for small vessels and detecting those with low-velocity flow.

Both CDI and Power Doppler may be used to generate the intraoperative sensor data. Either one or a combination of both of these imaging technologies can be coupled into the microscope system (e.g. via the system). The colors representing the speed and velocity of the blood flow within a certain area may be presented as an overlay (i.e. the visualization) on the eye piece or digital screen to provide surgeons with greater clinical confidence. Power Doppler imaging can be done in conjunction with three-dimensional imaging to provide volumetric information.

Doppler imaging can additionally be coupled with Optical coherence tomography (OCT) to provide a safe, non-invasive visualization of the different layers of the eye with real-time mapping of the flow in the vascular structures.

FIG. 3 shows a schematic diagram of different sensors and modalities being used in glaucoma surgery. FIG. 3 shows the surgical microscope (i.e. the optics carrier) 150, with microscope objective/lens 154, which is directed at a gonioprism 300, which redirects the optical path of the surgical microscope towards the eye 160. A non-invasive doppler transducer (probe) 120 can be coupled with the microscope either integrated as part of the optic carrier or as an extendable handpiece attached to the microscope system. FIG. 3 further shows the doppler probe 120, which is attached via a flexible arm 122 to the microscope 150. The probe may be held in position against the patient's eye during surgery with a flexible supporting arm extended from the microscope. An ultrasound gel 310 can be used as intermediary between the ocular surface and the probe tip, i.e. the doppler probe is brought into contact with the eye via ultrasound gel 310. FIG. 4 shows a schematic diagram of a view on an eye 160 through a gonioprism 300. FIG. 4 further shows a surgical instrument 400, as viewed directly and through the gonioprism 300.

Through the emission of high-frequency sound waves to the blood vessels and measuring the reflection the system may be able to measure and show movement of liquid through the vessels (e.g. the blood flow). A processing unit (e.g. the system 110) can change the intensity of sound waves into different colors to reflect the intensity of flow in real time during surgery. Additionally, a range control can be used to adjust the penetration depth of the ultrasound, allowing the system to either image the near the cornea and sclera or deeper to image the retinal structures.

By image recognition of the vascular tortuosity and thickness, combined with depth information, the system may be configured to match (i.e. align) the doppler image (i.e. the intraoperative sensor data) with the visual image from the microscope optics or camera (i.e. the visual intraoperative sensor data) and display a color overlay (e.g. the visualization), either as an image injection in the eyepiece or on the digital screen. In addition, the image can be reconstructed as three-dimensional image, to show the volume of the vessel when integrated with power Doppler.

Doppler imaging can additionally be coupled with Optical coherence tomography (OCT) to provide a safe, non-invasive visualization of the different layers of the eye with real-time mapping of the flow in the vascular structures. In this scenario, high-resolution tomographic images of tissue structure and blood flow simultaneously can be obtained during operation.

The presented concept may enable greater clinical confidence by providing a real-time intraoperative marker of a potential stent position within a given vessel during surgery. In addition, the doppler microscope can be used as a non-invasive method useful for the detection of retinal vascular structures or tumorous growths within the eye.

More details and aspects of the concept are mentioned in connection with the proposed concept or one or more examples described above or below (e.g. FIG. 1*a* to 2, 5). The concept may comprise one or more additional optional features corresponding to one or more aspects of the proposed concept or one or more examples described above or below.

Figure 5:
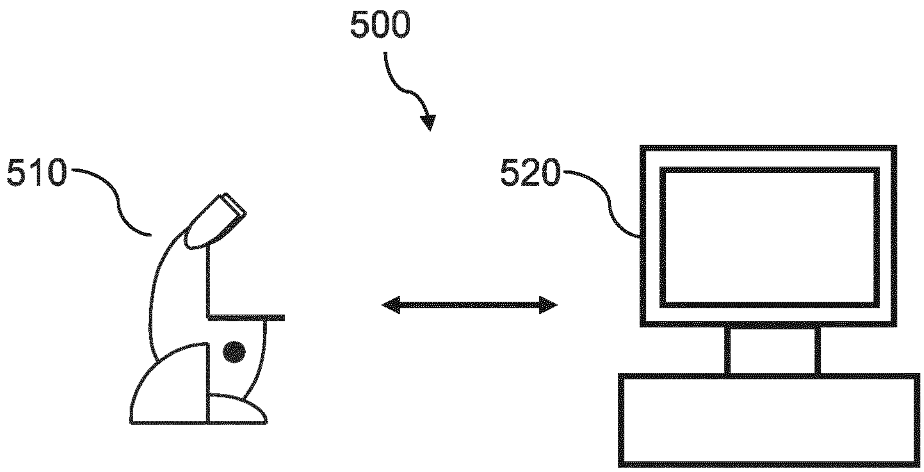
FIG. 5 shows a schematic diagram comprising a microscope and a computer system.

Some embodiments relate to a microscope comprising a system as described in connection with one or more of the FIGS. 1 to 4. Alternatively, a microscope may be part of or connected to a system as described in connection with one or more of the FIGS. 1 to 4. FIG. 5 shows a schematic diagram comprising a microscope and a computer system. FIG. 5 shows a schematic illustration of a system 500 configured to perform a method described herein. The system 500 comprises a microscope 510 and a computer system 520. The microscope 510 is configured to take images and is connected to the computer system 520. The computer system 520 is configured to execute at least a part of a method described herein. The computer system 520 may be configured to execute a machine learning algorithm. The computer system 520 and microscope 510 may be separate entities but can also be integrated together in one common housing. The computer system 520 may be part of a central processing system of the microscope 510 and/or the computer system 520 may be part of a subcomponent of the microscope 510, such as a sensor, an actor, a camera or an illumination unit, etc. of the microscope 510.

The computer system 520 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 520 may comprise any circuit or combination of circuits. In one embodiment, the computer system 520 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 520 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 520 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 520 may also include a display device, one or more speakers, and a keyboard and/or controller, which can include a mouse, trackball, touch screen, voice-recognition device, or any other device that permits a system user to input information into and receive information from the computer system 520.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a nontransitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

LIST OF REFERENCE SIGNS

100 Surgical microscope system
105 Base unit
110 System
112 Interface
114 One or more processors
116 One or more storage devices
120 Doppler-based imaging sensor
122 Flexible arm
130 Display device
132 Visualization
140 Optical Coherence Tomography Sensor
150 Surgical microscope
160 Eye
170 Arm
180 Steering handles
210 Obtaining intraoperative sensor data
220 Processing the intraoperative sensor data
230 Generating a visualization of a blood flow
240 Providing a display signal to a display device
300 Gonioprism
310 Ultrasound gel
400 Surgical instrument
500 System
510 Microscope
520 Computer system

The invention claimed is:

1. A system for a surgical microscope system, the system comprising one or more processors and one or more storage devices, wherein the system is configured to:

obtain intraoperative sensor data of at least a portion of an eye from a Doppler-based imaging sensor of the surgical microscope system;

process the intraoperative sensor data to determine information on blood flows within the eye;

generate a visualization of the blood flows; and provide a display signal to a display device of the surgical microscope system based on the visualization of the blood flows within the eye, wherein the system is configured to obtain intraoperative three-dimensional sensor data of a plurality of layers of the eye from a further sensor of the surgical microscope system, determine the plurality of layers of the eye within the intraoperative three-dimensional sensor data, and assign the blood flows to the plurality of layers of the eye, wherein the visualization is generated such that the blood flows within different layers are distinguishable in the same visualization, wherein the Doppler-based imaging sensor and the further sensor are separate sensors.

2. The system according to claim 1, wherein the system is configured to obtain the intraoperative three-dimensional sensor data from an optical coherence tomography sensor of the surgical microscope system.

3. The system according to claim 1, wherein the system is configured to obtain intraoperative visual sensor data of the eye from an optical imaging sensor of the surgical microscope system, determine an alignment between the intraoperative sensor data and the intraoperative visual sensor data, and to provide the display signal to the display device based on the alignment between the intraoperative sensor data and the intraoperative visual sensor data.

4. The system according to claim 3, wherein the system is configured to overlay the visualization over the intraoperative visual sensor data, and to provide the display signal comprising the intraoperative visual sensor data with the overlaid visualization to the display device.

5. The system according to claim 3, wherein the system is configured to provide the visualization without the intraoperative visual sensor data to the display device.

6. The system according to claim 1, wherein the intraoperative sensor data is intraoperative sensor data from a Power Doppler imaging sensor.

7. The system according to claim 1, wherein the intraoperative sensor data is intraoperative sensor data from a Color Doppler Imaging sensor.

8. A surgical microscope system comprising the system according to claim 1, a Doppler-based imaging sensor, and a display device.

9. The surgical microscope system according to claim 8, wherein the Doppler-based imaging sensor is a Color Doppler Imaging sensor, or wherein the Doppler-based imaging sensor is a Power Doppler sensor, and/or wherein the Doppler-based imaging sensor is configured to generate the intraoperative sensor data via a probe to be brought in contact with the eye.

10. The surgical microscope system according to claim 8, wherein the Doppler-based imaging sensor comprises a range control modality for adjusting the penetration depth of ultrasound emitted by the Doppler-based imaging sensor, wherein the system is configured to control the range control modality to adapt a depth of the intraoperative sensor data.

11. The system of claim 1, wherein the system is configured to determine an amount, a velocity, and/or a direction of the blood flows based on the intraoperative sensor data and generate the visualization such that the amount, the velocity, and/or the direction of the blood flows are visualized within the display signal.

12. The system of claim 11, wherein the amount, the velocity, and/or the direction of the blood flows are indicated by different colors, such that a first direction of a blood flow is indicated by a first range of colors and a second direction of the blood flow is indicated by a second range of colors, and a color within the first range of colors and the second range of colors represents an amount and/or a velocity of the blood flow in the respective direction.

13. A method for a surgical microscope system, the method comprising:

obtaining intraoperative sensor data of at least a portion of an eye from a Doppler-based imaging sensor of the surgical microscope system;

processing the intraoperative sensor data to determine information on blood flows within the eye;

obtaining intraoperative three-dimensional sensor data of a plurality of layers of the eye from a further sensor of the surgical microscope system;

determining the plurality of layers of the eye within the intraoperative three-dimensional sensor data;

assigning the blood flows to the plurality of layers of the eye, generating a visualization of the blood flows, wherein the visualization is generated such that the blood flows within different layers are distinguishable in the same visualization; and providing a display signal to a display device of the surgical microscope system based on the visualization of the blood flows within the eye, wherein the Doppler-based imaging sensor and the further sensor are separate sensors.

14. A non-transitory, computer-readable medium comprising a program code that, when the program code is executed on a processor, a computer, or a programmable hardware component, causes the processor, computer, or programmable hardware component to perform the method of claim 13.

15. The method of claim 13, wherein an amount, a velocity, and/or a direction of the blood flows are determined based on the intraoperative sensor data and the visualization is generated such that the amount, the velocity, and/or the direction of the blood flows are visualized within the display signal.

16. The method of claim 15, wherein the amount, the velocity, and/or the direction of the blood flows are indicated by different colors, such that a first direction of a blood flow is indicated by a first range of colors and a second direction of the blood flow is indicated by a second range of colors, and a color within the first range of colors and the second range of colors represents an amount and/or a velocity of the blood flow in the respective direction.

* * * * *